United States Patent
Han

(12) 
(10) Patent No.: US 6,708,353 B2
(45) Date of Patent: Mar. 23, 2004

(54) PROTECTIVE APPARATUS FOR HUMAN BACKBONES

(76) Inventor: Wan-Seok Han, #610-4, Shinsa-dong, Kangnam-ku, 135-894, Seoul (KR)

( * ) Notice: Subject to any disclaimer, the term of this patent is extended or adjusted under 35 U.S.C. 154(b) by 0 days.

(21) Appl. No.: 10/131,240

(22) Filed: Apr. 25, 2002

(65) Prior Publication Data

US 2003/0126684 A1 Jul. 10, 2003

(30) Foreign Application Priority Data

Jan. 4, 2002 (KR) .......................................... 2002-375

(51) Int. Cl.$^7$ ................................................ A47C 20/00
(52) U.S. Cl. ................................... 5/632; 5/630; 5/652
(58) Field of Search ........................... 5/630, 632, 690, 5/636, 652, 659, 655.3, 655.9

(56) References Cited

U.S. PATENT DOCUMENTS

| | | | | |
|---|---|---|---|---|
| 2,634,799 A | * | 4/1953 | Young | 267/81 |
| 3,719,185 A | * | 3/1973 | Hanes | 606/240 |
| 3,842,453 A | * | 10/1974 | Redfield | 5/643 |
| 4,602,765 A | * | 7/1986 | Loper et al. | 256/19 |
| 5,396,674 A | * | 3/1995 | Bolds | 5/633 |
| 5,507,049 A | * | 4/1996 | Lane | 5/484 |
| 5,530,974 A | * | 7/1996 | Rains et al. | 5/81.1 T |
| 5,675,850 A | * | 10/1997 | Schmitt | 5/630 |
| 5,824,013 A | * | 10/1998 | Allen | 606/240 |
| 6,067,679 A | * | 5/2000 | Rice | 5/630 |
| 6,253,400 B1 | * | 7/2001 | Rudt-Sturzenegger et al. | 5/655 |
| 6,360,388 B2 | * | 3/2002 | Langer | 5/632 |
| 6,367,105 B1 | * | 4/2002 | Farley | 5/630 |
| 6,449,788 B1 | * | 9/2002 | Nichols | 5/636 |

* cited by examiner

Primary Examiner—Teri Pham Luu
(74) Attorney, Agent, or Firm—Nath & Associates PLLC; Gary M. Nath

(57) ABSTRACT

A protective apparatus for human backbones is disclosed. This apparatus has an inside body, which is made of a fabric, such as a cotton fabric or a taffeta, and defines an interior space filled with an appropriate filler. An all-cotton fabric covers the inside body to form an outer cover of the apparatus, with two ends of the all-cotton fabric being fastened together using a zip-fastener or a Velcro fastener, thus forming a seamed junction. The apparatus has a columnar shape with a circular cross-section, a triangular cross-section, a rectangular cross-section, a hexagonal cross-section, or an octagonal cross-section. This apparatus properly aligns the spinal vertebrae of a user while sleeping or taking a rest.

2 Claims, 3 Drawing Sheets

PROTECTIVE APPARATUS FOR HUMAN BACKBONES

BACKGROUND OF THE INVENTION

1. Field of the Invention

The present invention relates, in general, to protective apparatuses for human backbones and, more particularly, to a columnar protective apparatus for human backbones, designed to protect the normal backbone of a user by preventing the backbone from being twisted or deformed when the user sleeps or takes a rest, or orthopedically correct the deformed backbone of a patient having spinal deformities to the desired normal and natural shape of the spine when the patient continuously uses the protective apparatus for a predetermined lengthy period of time while sleeping or taking a rest.

2. Description of the Prior Art

As well known to those skilled in the art, the human backbone protects the spinal cord, which is a soft, fatty and vascular tissue extending from the brain into the interior cavity of the backbone. The spinal cord is a part of the central nervous system, and connects the autonomic nervous system, branching from the spinal cord through the spinal nerves and innervating all the human organs, such as the eyes, nose, heart, stomach, viscera, kidney, and liver, to the brain that is the other part of the central nervous system. The spinal cord thus transfers external information obtained by the organs to the brain and transmits commands from the brain to the autonomic nervous system to control and coordinate the physical actions of the organs. The backbone also functions as a support, which helps to maintain the proper posture.

In a brief description, the human backbone functions as a spinal protector for protecting the spinal cord, which constitutes the central nervous system in combination with the brain, and controls and coordinates the vital actions of the human organs. The human backbone also functions as a support helping to maintain the body's posture. It is thus necessary for people to maintain the normal and natural shape of their backbones in an effort to preserve their health. The human backbones also function as girders supporting weight of the upper body.

Such a human backbone has a smoothly-curved S-shaped profile, and consists of four vertebral portions, that is: a cervical vertebral portion including the first to seventh cervical vertebrae; a thoracic vertebral portion including the first to twelfth thoracic vertebrae; a lumbar vertebral portion including the first to fifth lumbar vertebrae; and a sacral vertebral portion including the sacrum and the coccyx.

SUMMARY OF THE INVENTION

Accordingly, the present invention has been made keeping in mind the above problems occurring in the prior art, and an object of the present invention is to provide a protective apparatus for human backbones, which is appropriately determined in its dimensions, including the width and length, such that it effectively prevents the backbones of users, from infants to adults, from being twisted or deformed, and maintains the balanced body postures of the users.

Another object of the present invention is to provide a protective apparatus for human backbones, which has a columnar shape with a circular or polygonal cross-section suitable for preventing the normal backbone of a user, regardless of whether the user is an infant or an adult, from being twisted or deformed when the user sleeps or takes a rest, or suitable for orthopedically correcting the deformed backbone of a patient having spinal deformities to the desired normal and natural shape of the spine when the patient continuously uses the protective apparatus for a predetermined lengthy period of time.

A further object of the present invention is to provide a protective apparatus for human backbones, which is made of an appropriate suitable material.

In order to accomplish the above objects, the present invention provides a protective apparatus for infant or adult backbones, which is designed to have an appropriate shape and size suitable for use by an infant or adult user. A user lies on a support surface with the protective apparatus held in the user's arms while sleeping or taking a rest. The apparatus thus prevents the normal backbone from being twisted or deformed, or orthopedically corrects the deformed backbone to the desired normal and natural shape of the spine.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
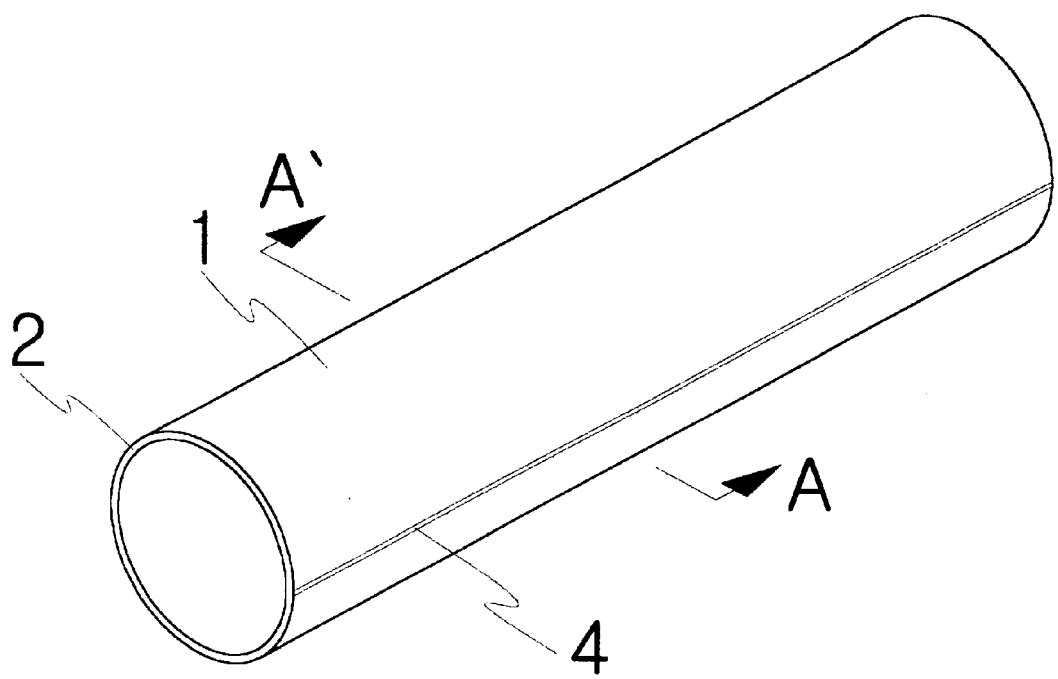
FIG. 1 is a perspective view of a columnar protective apparatus for human backbones having a circular cross-section in accordance with the primary embodiment of the present invention.

Reference should now be made to the drawings, in which the same reference numerals are used throughout the different drawings to designate the same or similar components.

Figure 2:
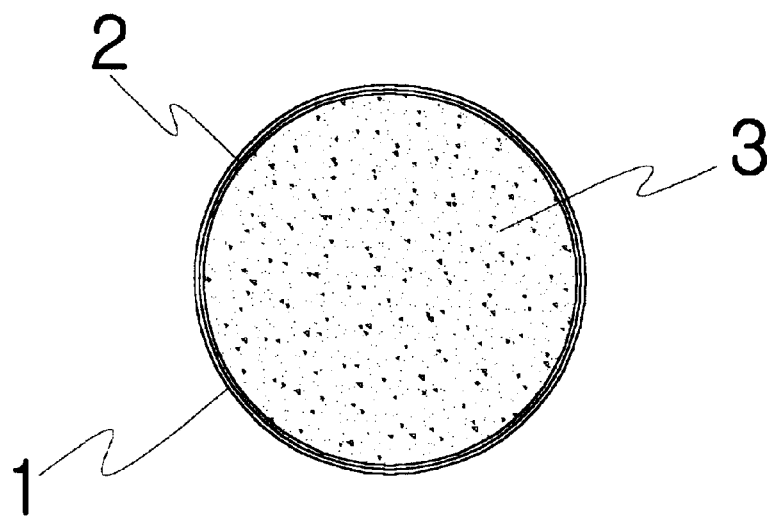
FIG. 2 is a sectional view of the protective apparatus taken along the line A–A' of FIG. 1.

FIGS. 1 and 2 show a columnar protective apparatus for human backbones having a circular cross-section in accordance with the primary embodiment of the present invention. As shown in the drawings, the protective apparatus for human backbones in accordance with the primary embodiment of this invention has a cylindrical columnar shape with a circular cross-section. This protective apparatus is filled in its interior space 3 with appropriate filler, selected from the group consisting of cotton, sponge, husks of rice, husks of buckwheat, mugwort, sawdust, wood chips, hardwood charcoals, loess, sands, pebbles, and artificial bio-ceramics. The interior space 3 of this protective apparatus is defined by an inside body 2, which is made of a fabric, such as a cotton fabric or a taffeta. The fabric inside body 2 is covered with an all-cotton fabric 1, which forms an outer cover of the protective apparatus. The two ends of the all-cotton fabric 1 are fastened together using a zip-fastener or a Velcro fastener, thus forming a seamed junction 4. FIG. 2 is a sectional view of the cylindrical columnar protective apparatus taken along the line A–A' of FIG. 1.

In the present invention, the protective apparatus may have a solid mandrel, made of wood or plastic, in place of the interior space 3. In such a case, it is not necessary to contain the filler in the apparatus.

In a modification of the preferred embodiment of this invention, the inside body 2 may be made of a plastic material, such as polyethylene (P.E) or polypropylene (P.P), in place of a fabric. In such a case, an air injection hole (not shown) is formed at an appropriate position of the protective apparatus having the plastic inside body so as to allow a user to fill the interior space 3 with air. In order to use the protective apparatus according to the above modification, air may be easily injected into the interior space 3 by the use of the mouth of a user or an air injecting machine. When the protective apparatus is out of use, it is possible to deflate the air-inflated apparatus by opening the air injection hole. The protective apparatus according to this modification is thus convenient to a user while using or carrying it.

Such protective apparatuses for human backbones of this invention may be produced in different sizes suitable for being separately used by infants and adults. The size of the protective apparatuses for infants is preferably set to dimensions of 3~8 cm (width)×40~90 cm (length), and more preferably, dimensions of 4.5 cm (width)×50 cm (length).

The size of the protective apparatuses for adults is preferably set to dimensions of 25~35 cm (width)×80~150 cm (length), and more preferably, dimensions of 30 cm (width)×100 cm (length).

Figure 3:
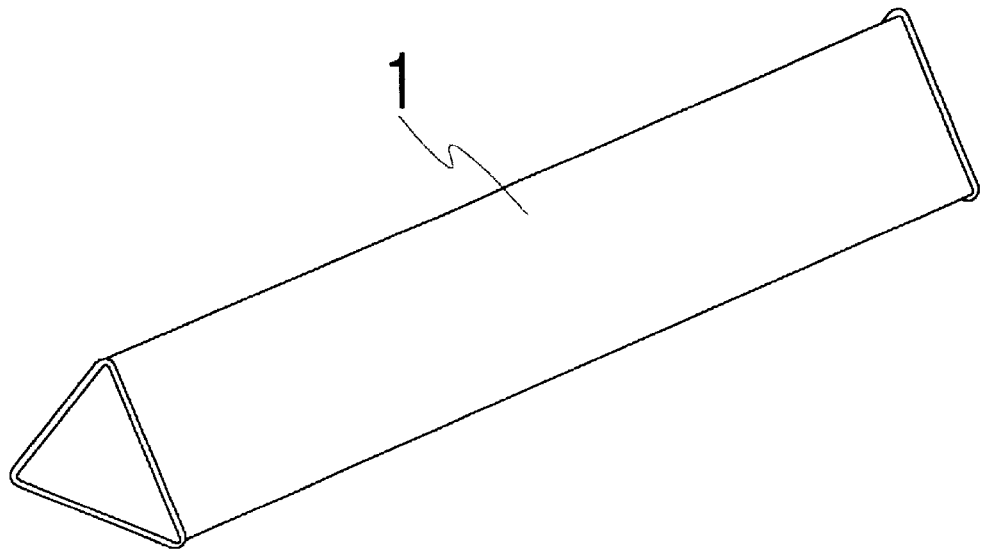
FIG. 3 is a perspective view of a columnar protective apparatus for human backbones having a triangular cross-section in accordance with the second embodiment of the present invention.
Figure 4:
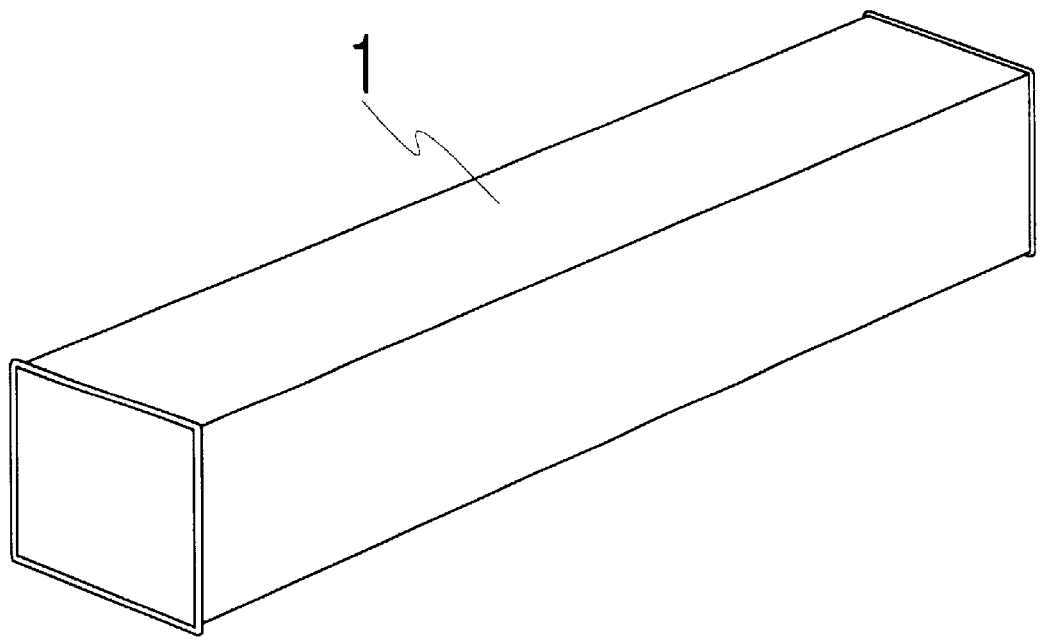
FIG. 4 is a perspective view of a columnar protective apparatus for human backbones having a rectangular cross-section in accordance with the third embodiment of the present invention.
Figure 5:
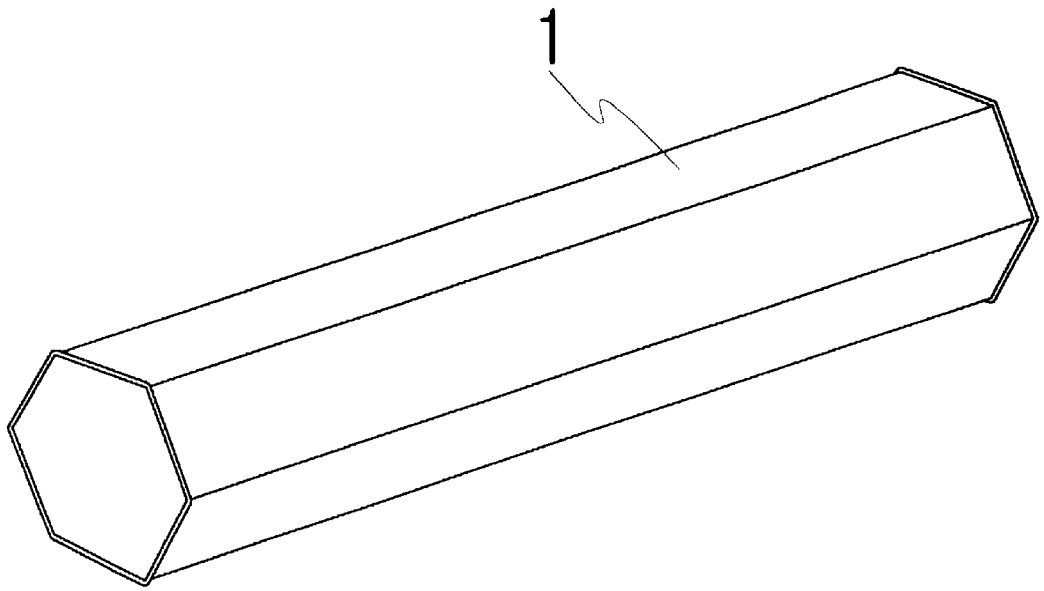
FIG. 5 is a perspective view of a columnar protective apparatus for human backbones having a hexagonal cross-section in accordance with the fourth embodiment of the present invention.
Figure 6:
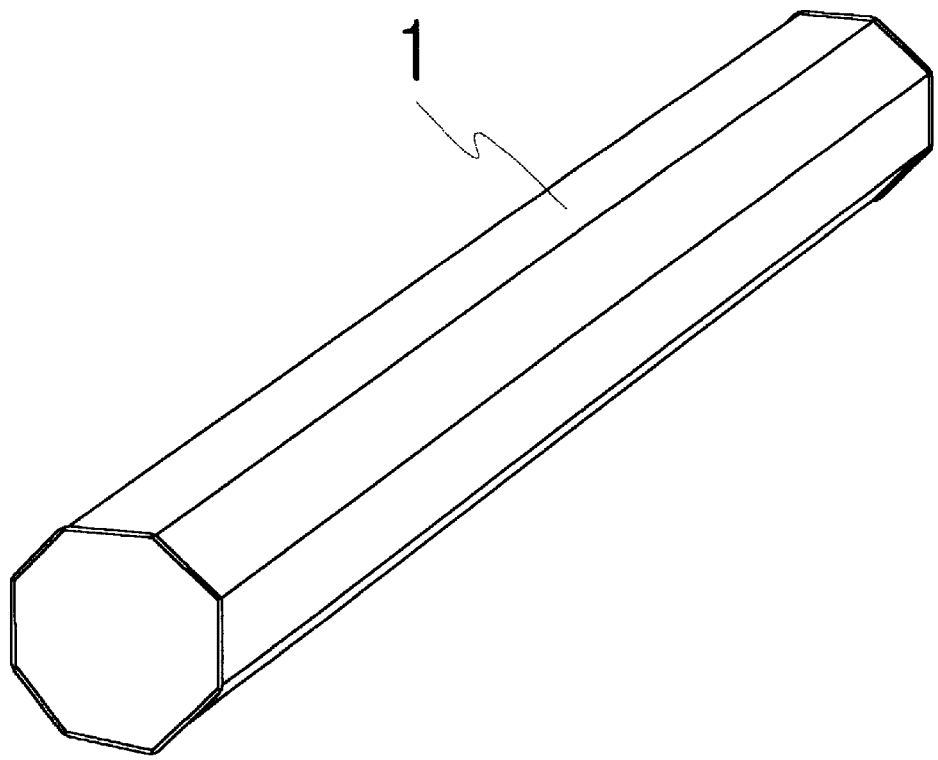
FIG. 6 is a perspective view of a columnar protective apparatus for human backbones having an octagonal cross-section in accordance with the fifth embodiment of the present invention.

When the inside body of the protective apparatus of this invention is made of plastic or wood in place of fabric, different from the primary embodiment, it is possible to produce a square columnar protective apparatus as shown in FIG. 3, a rectangular columnar protective apparatus as shown in FIG. 4, a hexagonal columnar protective apparatus as shown in FIG. 5, or an octagonal columnar protective apparatus as shown in FIG. 6. Of course, the cross-section of the columnar protective apparatus having such a plastic or wood inside body according to the modification of this invention is not limited to the above-mentioned cross-sections, but may be somewhat freely changed without affecting the functioning of this invention.

The operational effect of the protective apparatus for human backbones of this invention will be described herein below.

In order to use the protective apparatus of this invention for protecting the backbone when a user sleeps or takes a rest, the infant or adult user lies on a support surface, such as a flat floor or a mattress, while holding the protective apparatus in his/her arms and maintains the lying posture for a lengthy period of time. The protective apparatus thus protects the backbone of the user by preventing the cervical vertebrae, the thoracic vertebrae and the lumbar vertebrae from being twisted or deformed. That is, when a person unconsciously lies on his/her side while sleeping or taking a rest, the upper one of the two legs of the user excessively passes over the other leg, thus causing the vertebrae to be twisted or deformed. However, when lying on a support surface while holding the protective apparatus in one's arms as described above, the apparatus prevents one of the two legs of a user from excessively passing over the other leg, and properly aligns the vertebrae of the user's spine. The protective apparatus, held in the arms of a user lying on a support surface while sleeping or taking a rest, also prevents the torso from being excessively bent, thus more effectively protecting the vertebrae of the user's spine.

As described above, the present invention provides a protective apparatus for human backbones. When a user, who wants to sleep or take a rest, lies on a support surface, such as a flat floor or a mattress, while holding the protective apparatus in his/her arms, it is possible to prevent the torso from being excessively bent toward the support surface, and prevent one of the two legs of the user from excessively passing over the other leg. The protective apparatus thus protects the backbone of a user by preventing the seven cervical vertebrae, the twelve thoracic vertebrae and the five lumbar vertebrae from being twisted or deformed. Therefore, this apparatus maintains the balanced and properly aligned spine and preserves human health, thus having high market competitiveness in the health promotion industry. A variety of diseases of the human body result from spinal deformities, which are caused by the twisting of the spine while sleeping. However, the protective apparatus of this invention properly aligns the vertebrae of a user, and maintains the body's proper posture, regardless of whether the user is an infant or an adult, when the user uses the apparatus while sleeping or taking a rest. It is thus evident that this apparatus is a highly functional instrument capable of effectively preventing a variety of diseases caused by hereditary or acquired spinal deformity.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A method of protecting and correcting human backbones comprising the steps of:

providing a protective apparatus made of wood or plastic having a cross-section selected from the group consisting of a triangular cross-section, rectangular cross-section, hexagonal cross-section and octagonal cross-section, wherein the apparatus has dimensions of 3~8 cm (width)×40~90 cm (length) for infants; and embracing or resting one leg and one arm on said protective apparatus while sleeping or taking a rest.

2. A method of protecting and correcting human backbones comprising the steps of:

providing a protective apparatus made of wood or plastic having a cross-section selected from the group consisting of a triangular cross-section, rectangular cross-section, hexagonal cross-section and octagonal cross-section, wherein the apparatus has dimensions of 25~35 cm (width)×80~150 cm (length) for adults; and embracing or resting one leg and one arm on said protective apparatus while sleeping or taking a rest.

* * * * *